United States Patent
Li et al.

(10) Patent No.: US 12,297,468 B2
(45) Date of Patent: May 13, 2025

(54) PAPN MUTANT AND COMPOSITION FOR SITE-DIRECTED MODIFICATION OF PAPN GENE AND APPLICATION THEREOF

(71) Applicant: AGSINO GENSOURCES CO., LTD., Shenzhen (CN)

(72) Inventors: Kui Li, Shenzhen (CN); Yulian Mu, Shenzhen (CN); Lei Huang, Shenzhen (CN)

(73) Assignee: AGSINO GENSOURCES CO., LTD., Shenzhen (CN)

( * ) Notice: Subject to any disclaimer, the term of this patent is extended or adjusted under 35 U.S.C. 154(b) by 0 days.

(21) Appl. No.: 18/490,030

(22) Filed: Oct. 19, 2023

(65) Prior Publication Data
US 2024/0417711 A1    Dec. 19, 2024

(30) Foreign Application Priority Data
Jun. 14, 2023    (CN) .......................... 202310706300.0

(51) Int. Cl.
| | |
|---|---|
| *C12N 9/48* | (2006.01) |
| *A01K 67/0275* | (2024.01) |
| *C07H 21/04* | (2006.01) |
| *C12N 15/90* | (2006.01) |

(52) U.S. Cl.
CPC .......... *C12N 9/485* (2013.01); *A01K 67/0275* (2013.01); *C07H 21/04* (2013.01); *C12N 15/907* (2013.01); *C12Y 304/11002* (2013.01); *A01K 2217/05* (2013.01); *A01K 2227/108* (2013.01); *C12N 2310/20* (2017.05)

(58) Field of Classification Search
CPC .. C12N 9/485; C12N 15/907; C12N 2310/20; A01K 67/0275; A01K 2217/05; A01K 2227/108; C07H 21/04; C12Y 304/11002
USPC ........... 435/212, 226, 455; 800/17; 536/23.2
See application file for complete search history.

(56) References Cited

PUBLICATIONS

Whitworth (2019) Transgenic Res., vol. 28:21-32.*
Tusell et al. (2007) J. Virol., vol. 81(3):1261-1273.*
Yu et al. (2021) Archives Virol., vol. 166:157-165.*
Stephenson et al. (2013) J. Mol. Evol., vol. 77:159-169.*

* cited by examiner

*Primary Examiner* — Anne Marie S Wehbe
(74) *Attorney, Agent, or Firm* — HAUPTMAN HAM, LLP

(57) ABSTRACT

The present invention provides a pAPN mutant and a composition for site-directed modification of pAPN gene and application thereof, involving the field of gene editing technology. The mutated pAPN mutant with an alanine at position 734 can maintain its normal expression, while reducing the ability of a host expressing the pAPN mutant to specifically bind to TGEV, which has important scientific and practical significance in pig disease resistance breeding.

2 Claims, 5 Drawing Sheets
Specification includes a Sequence Listing.

SEQUENCE LISTING

```
Sequence total quantity: 15
SEQ ID NO: 1            moltype = AA  length = 963
FEATURE                 Location/Qualifiers
source                  1..963
                        mol_type = protein
                        organism = Sus scrofa
SEQUENCE: 1
MAKGFYISKA LGILGILLGV AAVATIIALS VVYAQEKNKN AEHVPQAPTS PTITTTAAIT    60
LDQSKPWNRY RLPTTLLPDS YNVTLRPYLT PNADGLYIFK GKSIVRFICQ EPTDVIIIHS   120
KKLNYTTQGH MVVLRGVGDS QVPEIDRTEL VELTEYLVVH LKGSLQPGHM YEMESEFQGE   180
LADDLAGFYR SEYMEGNVKK VLATTQMQST DARKSFPCFD EPAMKATFNI TLIHPNNLTA   240
LSNMPPKGSS TPLAEDPNWS VTEFETTPVM STYLLAYIVS EFQSVNETAQ NGVLIRIWAR   300
PNAIAEGHGM YALNVTGPIL NFFANHYNTP YPLPKSDQIA LPDFNAGAME NWGLVTYREN   360
ALLFDPQSSS ISNKERVVTV IAHELAHQWF GNLVTLAWWN DLWLNEGFAS YVEYLGADHA   420
EPTWNLKDLI VPGDVYRVMA VDALASSHPL TTPAEEVNTP AQISEMFDSI SYSKGASVIR   480
MLSNFLTEDL FKEGLASYLH AFAYQNTTYL DLWEHLQKAV DAQTSIRLPD TVRAIMDRWT   540
LQMGFPVITV DTKTGNISQK HFLLDSESNV TRSSAFDYLW IVPISSIKNG VMQDHYWLRD   600
VSQAQNDLFK TASDDWVLLN INVTGYFQVN YDEDNWRMIQ HQLQTNLSVI PVINRAQVIY   660
DSFNLATAHM VPVTLALDNT LFLNGEKEYM PWQAALSSLS YFSLMFDRSE VYGPMKKYLR   720
KQVEPLFQHF ETLAKNWTER PENLMDQYSE INAISTACSN GLPQCENLAK TLFDQWMSDP   780
ENNPIHPNLR STIYCNAIAQ GGQDQWDFAW GQLQQAQLVN EADKLRSALA CSNEVWLLNR   840
YLGYTLNPDL IRKQDATSTI NSIASNVIGQ PLAWDFVQSN WKKLFQDYGG GSFSFSNLIQ   900
GVTRRFSSEF ELQQLEQFKK NNMDVGFGSG TRALEQALEK TKANIKWVKE NKEVVLNWFI   960
EHS                                                                963

SEQ ID NO: 2            moltype = RNA  length = 20
FEATURE                 Location/Qualifiers
source                  1..20
                        mol_type = other RNA
                        organism = synthetic construct
SEQUENCE: 2
ctagaaatac ctcaggaagc                                                20

SEQ ID NO: 3            moltype = RNA  length = 20
FEATURE                 Location/Qualifiers
source                  1..20
                        mol_type = other RNA
                        organism = synthetic construct
SEQUENCE: 3
cgagcgccca gaaaatctga                                                20

SEQ ID NO: 4            moltype = DNA  length = 1000
FEATURE                 Location/Qualifiers
source                  1..1000
                        mol_type = other DNA
                        organism = synthetic construct
SEQUENCE: 4
cctttgagca cagtctggcc ttgtgcgagg cctttagcct ctggcctctt gctcctgtag    60
ccattagctc ttgctacatc tgcccaccca catcagaggc tccatgggtc tccagatgac   120
tcaggcatga gtctcttctt tgaagctatt tttagggctg catcctcggc atgtggaggt   180
tcccaagcta ggggttgaat cggagctgta gccgccagcc tacaccacag ccacagcaca   240
acgggatccg agccacatct gcgacctaca ccacagctca cagcaatgcc agatccttaa   300
cccactgagt ggggccaggg ttgaacccat gtcctcatgt ttcccagtca gattcgtttc   360
tgctgtgcca tgacgggaac tctggaactt cctctttgaa gctctttatg ttttgttctt   420
gtttttttgtt tttgtttttc tagaaatacc tcaggaagca agtcgaaccc ctcttccaac   480
atttcgaaac tctcgccaaa aactggaccg agcgcccaga aaacttaatg gaccagtgag   540
tatgagctcg cttggtctgg agatcatggg tggtgcaggt agcctgacct gggggcccat   600
agcaagtcca gcagcatcct ctctggagct cccaactcct ggccggacca gggccacagt   660
cagggagagc gacccctccc aaccccactc ccggcccag gagtagggac tctgctctga   720
ggctctgtgt ggcctatgaa ccatctggcc tcttgggca aaggaccaaa ctgaacctct   780
gagggtccct caccgcatg tgaggttct aggtgttaaa gctggggctg gagcctgtgc   840
cagccctccc caggctgccc aagggcaaga agcaaagaag ggaacccaaa ggtggctggt   900
gggctatacc tgcagagtgc gggtctgcct ccctgttggg agttgtgtgt cagcagggga   960
gtcttggtca gcgtcaggtc caggcgtgct gacagagtgt                        1000
```

| SEQ ID NO: 5 | moltype = DNA length = 2892 |
| FEATURE | Location/Qualifiers |
| source | 1..2892 |
| | mol_type = other DNA |
| | organism = Sus scrofa |

SEQUENCE: 5

```
atggccaagg gattctacat ttccaaggcc ctgggcatcc tgggcatcct cctcggcgtg    60
gcggccgtgg ccaccatcat cgctctgtct gtggtgtacg cccaggagaa gaacaagaat   120
gccgagcatg tcccccaggc cccccacgtcg cccaccatca ccaccacagc cgccatcacc   180
ttggaccaga gcaagccgtg gaaccggtac cgcctaccca aacgctgtt gcctgattcc    240
tacaacgtga cgctgagacc ctacctcact cccaacgcgg atggcctgta catcttcaag   300
ggcaaaagca tcgtccgctt catctgccag gagcccaccg atgtcatcat catccatagc   360
aagaagctca actacaccac ccaggggcac atggtggtcc tgcggggcgt gggggactcc   420
caggtcccag agatcgacag gactgagctg gtagagctca ctgagtacct ggtggtccac   480
ctcaagggct cgctgcagcc cggccacatg tacgagatgg agagtgaatt ccaggggggaa   540
cttgccgacg acctggcagg cttctaccgc agcgagtaca tggagggcaa cgtcaaaaag   600
gtgctggcca cgacacagat gcagtctaca gatgcccgga atccttccc atgctttgac    660
gagccagcca tgaaggccac gttcaacatc ctctcatcc accctaacaa cctcacggcc   720
ctgtccaata tgccgcccaa aggttccagc accccacttg cagaagaccc caactggtct   780
gtcactgagt tcgaaaccac acctgtgatg tccacgtacc ttctggccta catcgtgagc   840
gagttccaga gcgtgaatga aacgcccaa aatggcgtcc tgatccggat ctgggctcgg    900
cctaatgcaa ttgcagaggg ccatggcatg tatgccctga atgtgacagg tcccatccta   960
aacttctttg ccaatcatta taatacaccc taccccactcc ccaaatccga ccagattgcc  1020
ttgcccgact tcaatgccgg tgccatggag aactggggggc tggtgaccta ccgggagaac  1080
gcgctgctgt ttgacccaca gtcctcctcc atcagcaaca aagagcgagt tgtcactgtg  1140
attgctcacg agctggccca ccagtggttt ggcaacctgc tggccctgct ggtggaat    1200
gacctgtggc tgaatgaggg cttttgcctcc tatgtggagt acctgggtgc tgaccacga   1260
gagcccacct ggaatctgaa agacctcatc gtgccaggcg acgtgtaccg agtgatggct  1320
gtggatgctc tggcttcctc ccaccgctg accacccctg ctgaggaggt caacacacct   1380
gcccagatca gcgagatgtt tgactcagat cctacagga gggagcctc ggttatcgaa   1440
atgctctcca acttcctgac tgaggacctg ttcaaggag gcctggcgtc ctacttgcat  1500
gcctttgcct atcagaacac cacctacctg gacctgtggg agcacctgca gaaggctgtg  1560
gatgctcaga cgtccatcag gctgccagac actgtgagag ccatcatgga tcgatggacc  1620
ctgcagatgg gcttcccgt catcaccgtg gacaccaaga caggaaacat ctcacagaag  1680
cacttcctcc tcgactccga atccaacgtc acccgctcct cagcgttcga ctacctctgg  1740
attgttccca tctcatctat taaaaatggt gtgatgcagg atcactactg gctgcgggat  1800
gtttcccaag cccagaatga tttgttcaaa accgcatcgg acgattgggt cttgctgaac  1860
atcaacgtga caggctattt ccaggtgaac tacgacgagg acaactggag gatgattcag  1920
catcagctgc agacaaacct gtcggtcatc cctgtcatca atcgggctca ggtcatctac  1980
gacagcttca acctgccac tgcccacatg gtccctgtca ccctggctct ggacaacacc   2040
ctcttcctga acggagagaa agagtacatg ccctggcagg ccgccctgag cagcctgagc   2100
tacttcagcc tcatgttcga ccgctccgag gtctatggcc ccatgaagaa ataccctcagg  2160
aagcaggtca acccctctt ccaacattc gaaactctca ctaaaaactg gaccgagcgc   2220
ccagaaaatc tgatggacca gtacagtgag attaatgcca tcagcactgc ctgctcaat  2280
ggattgcctc aatgtgagaa tctgccaag acccttttcg accagtggat gagcgaccca  2340
gaaaataacc cgatccaccc caacctgcgg tccaccatct actgcaatgc catagcccag  2400
gcggcagg accagtggga cttttgcctgg gggcagttac aacaagcca gctggtaaat   2460
gaggccgaca aactccgctc agcgctggcc tgcagcaacg aggtctggct cctgaacagg   2520
tacctggggtt acaccctgaa cccggaccctc attcggaagc aagacgccac ctccactatt   2580
aacagcattg ccagcaatgt catcgggcag cctctggcct gggattttgt ccagagcaac   2640
tggaagaagc tcttcagga ctatgcggt ggttcctttc ccttctccaa cctcatccag   2700
ggtgtgaccc gaagattctc ctctgagttt gagctgcagc agctggagca gttcaagaag   2760
aacaacatgg atgtgggctt cggctccggc acccgggctc tggagcaagc cctggagaag   2820
accaaggcca acatcaagtg ggtgaaggag aacaaggagt ggtgttgaa ttggttcata   2880
gagcacagct aa                                                       2892
```

| SEQ ID NO: 6 | moltype = DNA length = 2892 |
| FEATURE | Location/Qualifiers |
| source | 1..2892 |
| | mol_type = other DNA |
| | organism = synthetic construct |

SEQUENCE: 6

```
atggccaagg gattctacat ttccaaggcc ctgggcatcc tgggcatcct cctcggcgtg    60
gcggccgtgg ccaccatcat cgctctgtct gtggtgtacg cccaggagaa gaacaagaat   120
gccgagcatg tcccccaggc cccccacgtcg cccaccatca ccaccacagc cgccatcacc   180
ttggaccaga gcaagccgtg gaaccggtac cgcctaccca aacgctgtt gcctgattcc    240
tacaacgtga cgctgagacc ctacctcact cccaacgcgg atggcctgta catcttcaag   300
ggcaaaagca tcgtccgctt catctgccag gagcccaccg atgtcatcat catccatagc   360
aagaagctca actacaccac ccaggggcac atggtggtcc tgcggggcgt ggggactcc    420
caggtcccag agatcgacag gactgagctg gtagagctca ctgagtacct ggtggtccac   480
ctcaagggct cgctgcagcc cggccacatg tacgagatgg agagtgaatt ccaggggggaa   540
cttgccgacg acctggcagg cttctaccgc agcgagtaca tggagggcaa cgtcaaaaag   600
gtgctggcca cgacacagat gcagtctaca gatgcccgga atccttccc atgctttgac    660
gagccagcca tgaaggccac gttcaacatc ctctcatcc accctaacaa cctcacggcc   720
ctgtccaata tgccgcccaa aggttccagc accccacttg cagaagaccc caactggtct   780
gtcactgagt tcgaaaccac acctgtgatg tccacgtacc ttctggccta catcgtgagc   840
gagttccaga gcgtgaatga aacgcccaa aatggcgtcc tgatccggat ctgggctcgg    900
cctaatgcaa ttgcagaggg ccatggcatg tatgccctga atgtgacagg tcccatccta   960
aacttctttg ccaatcatta taatacaccc taccccactcc ccaaatccga ccagattgcc  1020
```

```
ttgcccgact tcaatgccgg tgccatggag aactgggggc tggtgaccta ccgggagaac  1080
gcgctgctgt ttgacccaca gtcctcctcc atcagcaaca aagagcgagt tgtcactgtg  1140
attgctcacg agctggccca ccagtggttt ggcaacctgg tgaccctggc ctggtggaat  1200
gacctgtggc tgaatgaggg ctttgcctcc tatgtggagt acctgggtgc tgaccacgca  1260
gagcccacct ggaatctgaa agacctcatc gtgccaggcg acgtgtaccg agtgatggct  1320
gtggatgctc tggcttcctc ccaccgctg accaccctg ctgaggaggt caacacacct  1380
gcccagatca gcgagatgtt tgactccatc tcctacagca agggagcctc ggttatcagg  1440
atgctctcca acttcctgac tgaggacctg ttcaaggagg gcctggcgtc ctacttgcat  1500
gcctttgcct atcagaacac cacctacctg gacctgtggg agcacctgca gaaggctgtg  1560
gatgctcaga cgtccatcag gctgccagac actgtgagag ccatcatgga tcgatggacc  1620
ctgcagatgg gcttccccgt catcaccgtg gacaccaaga caggaaacat ctcacagaag  1680
cacttcctcc tcgactccga atccaacgtc acccgctcct cagcgttcga ctacctctgg  1740
attgttccca tctcatctat taaaaatggt gtgatgcagg atcactactg gctgcgggat  1800
gtttcccaag cccagaatga tttgttcaaa accgcatcgg acgattgggt cttgctgaac  1860
atcaacgtga caggctattt ccaggtgaac tacgacgagg acaactggag gatgattcag  1920
catcagctgc agacaaacct gtcggtcatc cctgtcatca atcgggctca ggtcatctac  1980
gacagcttca acctggccac tgcccacatg gtccctgtca cctggctct ggacaacacc  2040
ctcttcctga acggagagaa agagtacatg ccctggcagg cgccctgag cagcctgagc  2100
tacttcagcc tcatgttcga ccgctccgag gtctatggcc ccatgaagaa atacctcagg  2160
aagcaggtcg aaccctctt ccaagccttc gaaactctca ctaaaaactg gaccgagcgc  2220
ccagaaaatc tgatggacca gtacagtgag attaatgcca tcagcactgc ctgctccaat  2280
ggattgcctc aatgtgagaa tctggccaag accctttcg accagtggat gagcgaccca  2340
gaaaataacc cgatccaccc caacctgcgg tccaccatct actgcaatgc catagcccag  2400
ggcggccagg accagtggga ctttgcctgg gggcagttac aacaagccca gctggtaaat  2460
gaggccgaca aactccgctc agcgctggcc tgcagcaacg aggtctggct cctgaacagg  2520
tacctgggtt acaccctgaa cccggacctc attcggaagc aagcgccac ctccactatt  2580
aacagcattg ccagcaatgt catcgggcag cctctggcct gggattttgt ccagagcaac  2640
tggaagaagc tctttcagga ctatggccgt ggttccttct ccttctccaa cctcatccag  2700
ggtgtgaccc gaagattctc ctctgagttt gagctgcagc agctggagca gttcaagaag  2760
aacaacatgg atgtgggctt cggctccggc acccgggctc tggagcaagc cctggagaag  2820
accaaggcca acatcaagtg ggtgaaggag aacaaggagg tggtgttgaa ttggttcata  2880
gagcacagct aa                                                      2892

SEQ ID NO: 7           moltype = DNA    length = 2892
FEATURE                Location/Qualifiers
source                 1..2892
                       mol_type = other DNA
                       organism = synthetic construct
SEQUENCE: 7
atggccaagg gattctacat ttccaaggcc ctgggcatcc tggcatcct cctcggcgtg    60
gcggccgtgg ccaccatcat cgctctgtct gtggtgtacg cccaggagaa gaacaagaat   120
gccgagcatg tcccccaggc ccccacgtcg cccaccatca ccaccacagc cgccatcacc   180
tggaccagag gcaagccgtg gaaccggtac cgcctaccca caacgctgtt gcctgattcc   240
tacaacgtga cgctgagacc ctacctcact cccaacgcgg atggcctgta catcttcaag   300
ggcaaaagca tcgtccgctt catctgccag gagcccaccg atgtcatcat catccatagc   360
aagaagctca actacaccac ccaggggcac atggtggtcc tgcggggcgt ggggggactcc   420
caggtcccag agatcgacag gactgagctg gtagagctca ctgagtacct ggtggtccac   480
ctcaagggct cgctgcagcc cggccacatg tacgagatgg agagtgaatt ccagggggaa   540
cttgccgacg acctggcagg cttctaccgc agcgagtaca tggagggcaa cgtcaaaaag   600
gtgctggcca cgacacagat gcagtctaca gatgcccgga atccttccc atgctttgac   660
gagccagcca tgaaggccac gttcaacatc actctcatcc accctaacaa cctcacggcc   720
ctgtccaata tgccgcccaa aggttccagc accccacttg cagaagaccc caactggtct   780
gtcactgagt cgaaaccacc acctgtgatg tccacgtacc ttctggccta tcgtgagc   840
gagttccaga gcgtgaatga aacggccaa atggcgtcc tgatccggat ctgggctcgg   900
cctaatgcaa ttgcagaggg ccatggcatg tatgccctga atgtgacagg tcccatccta   960
aacttctttg ccaatcatta taatacaccc tacccactcc ccaaatccga ccagattgcc  1020
ttgcccgact tcaatgccgg tgccatggag aactgggggc tggtgaccta ccgggagaac  1080
gcgctgctgt ttgacccaca gtcctcctcc atcagcaaca aagagcgagt tgtcactgtg  1140
attgctcacg agctggccca ccagtggttt ggcaacctgg tgaccctggc ctggtggaat  1200
gacctgtggc tgaatgaggg ctttgcctcc tatgtggagt acctgggtgc tgaccacgca  1260
gagcccacct ggaatctgaa agacctcatc gtgccaggcg acgtgtaccg agtgatggct  1320
gtggatgctc tggcttcctc ccaccgctg accaccctg ctgaggaggt caacacacct  1380
gcccagatca gcgagatgtt tgactccatc tcctacagca agggagcctc ggttatcagg  1440
atgctctcca acttcctgac tgaggacctg ttcaaggagg gcctggcgtc ctacttgcat  1500
gcctttgcct atcagaacac cacctacctg gacctgtggg agcacctgca gaaggctgtg  1560
gatgctcaga cgtccatcag gctgccagac actgtgagag ccatcatgga tcgatggacc  1620
ctgcagatgg gcttccccgt catcaccgtg gacaccaaga caggaaacat ctcacagaag  1680
cacttcctcc tcgactccga atccaacgtc acccgctcct cagcgttcga ctacctctgg  1740
attgttccca tctcatctat taaaaatggt gtgatgcagg atcactactg gctgcgggat  1800
gtttcccaag cccagaatga tttgttcaaa accgcatcgg acgattgggt cttgctgaac  1860
atcaacgtga caggctattt ccaggtgaac tacgacgagg acaactggag gatgattcag  1920
catcagctgc agacaaacct gtcggtcatc cctgtcatca atcgggctca ggtcatctac  1980
gacagcttca acctggccac tgcccacatg gtccctgtca cctggctct ggacaacacc  2040
ctcttcctga acggagagaa agagtacatg ccctggcagg cgccctgag cagcctgagc  2100
tacttcagcc tcatgttcga ccgctccgag gtctatggcc ccatgaagaa atacctcagg  2160
aagcaggtcg aaccctctt ccaacatttc gaaactctcg ccaaaaactg gaccgagcgc  2220
ccagaaaatc tgatggacca gtacagtgag attaatgcca tcagcactgc ctgctccaat  2280
ggattgcctc aatgtgagaa tctggccaag accctttcg accagtggat gagcgaccca  2340
gaaaataacc cgatccaccc caacctgcgg tccaccatct actgcaatgc catagcccag  2400
```

```
ggcggccagg accagtggga cttttgcctgg gggcagttac aacaagccca gctggtaaat   2460
gaggccgaca aactccgctc agcgctggcc tgcagcaacg aggtctggct cctgaacagg   2520
tacctgggtt acaccctgaa cccggacctc attcggaagc aagacgccac ctccactatt   2580
aacagcattg ccagcaatgt catcgggcag cctctggcct gggattttgt ccagagcaac   2640
tggaagaagc tctttcagga ctatggcggt ggttccttct ccttctccaa cctcatccag   2700
ggtgtgaccc gaagattctc ctctgagttt gagctgcagc agctggagca gttcaagaag   2760
aacaacatgg atgtgggctt cggctccggc acccgggctc tggagcaagc cctggagaag   2820
accaaggcca acatcaagtg ggtgaaggag aacaaggagg tggtgttgaa ttggttcata   2880
gagcacagct aa                                                        2892

SEQ ID NO: 8          moltype = DNA   length = 2892
FEATURE               Location/Qualifiers
source                1..2892
                      mol_type = other DNA
                      organism = synthetic construct
SEQUENCE: 8
atggccaagg gattctacat ttccaaggcc ctgggcatcc tgggcatcct cctcggcgtg     60
gcggccgtgg ccaccatcat cgctctgtct gtggtgtacg cccaggagaa gaacaagaat    120
gccgagcatg tccccaggc ccccacgtcg cccaccatca ccaccacagc cgccatcacc    180
ttggaccaga gcaagccgtg gaaccggtac cgcctaccca aacgctgtt gcctgattcc    240
tacaacgtga cgctgagacc ctacctcact cccaacgcgg atggcctgta catcttcaag    300
gcaaaagca tcgtccgctt catctgccag gagcccaccg atgtcatcat catccatagc    360
aagaagctca actacaccac ccaggggcac atggtggtcc tgcggggcgt ggggactcc     420
caggtcccag agatcgacag gactgagctg gtagagctca ctgagtacct ggtggtccac    480
ctcaagggct cgctgcagcc cggccacatg tacgagatgg agagtgaatt ccagggggaa    540
cttgccgacg acctggcagc cttctaccgc agcagtaca tggagggcaa cgtcaaaaag    600
gtgctggcca cgacacagat gcagtctaca gatgccggga aatccttccc atgctttgac    660
gagccagcca tgaaggccac gttcaacatc actctcatcc accctaacaa cctcacggcc    720
ctgtccaata tgccgcccaa aggttccagc accccacttg cagaagaccc caactggtct    780
gtcactgagt tcgaaaccac acctgtgatg tccacgtact ttctggccta catcgtgct    840
gagttccaga gcgtgaatga aacggcccaa aatggcgtcc tgatccggat ctgggctcgg    900
cctaatgcaa ttgcagaggg ccatggcatg tatgccctga atgtgacagg tcccatccta    960
aacttctttg ccaatcatta atatacaccc tacccactcc caaatccga ccagattgcc    1020
ttgcccgact tcaatgccgg tgccatggag aactgggggc tggtgactca ccgggagaac    1080
gcgctgctgt ttgacccaca gtcctcctcc atcagcaaca aagagcgagt tgtcactgtg    1140
attgctcacg agctggccca ccagtggttt ggcaacctgg tgaccctggc ctggtggaat    1200
gacctgtggc tgaatgaggg cttttgcctcc tatgtggagt acctgggtgc tgaccacgca    1260
gagcccacct ggaatctgaa agacctcatc gtgccaggcg acgtgtaccg agtgatggct    1320
gtggatgctc tggcttcctc ccacccgctg accaccctg ctgaggaggt caacacacct    1380
gcccagatca gcgagatgtt tgactccatc tcctacagca agggagcctc ggttatcagg    1440
atgctctcca acttcctgac tgaggacctg ttcaaggagg gcctggctgc ctacttgcat    1500
gccttttgcct atcagaacac cacctacctg gacctgtggg agcacctgca gaaggctgtg    1560
gatgctcaga cgtccatcag gctgccagac actgtgagga ccatcatgga tcgatggacc    1620
ctgcagatgg gcttccccgt catcaccgtg gacaccaaga caggaaacat ctcacagaag    1680
cacttcctcc tcgactccga atccaacgtc cccgctcct cagcgttcga ctacctctgg    1740
attgttccca tctcatctat taaaaatggt gtgatgcagg atcactactg gctgcgggat    1800
gtttcccaag cccagaatga tttgttcaaa accgcatcgg acgattgggt cttgctgaac    1860
atcaacgtga caggctattt ccaggtgaac tacgacgagg acaactggag gatgattcag    1920
catcagctgc agacaaacct gtcggtcatc cctgtcatca atcgggctca ggtcatctac    1980
gacagcttca acctggccac tgcccacatg gtccctgtca ccctggctctt ggacaacacc    2040
ctcttcctga acggagagaa agagtacatg ccctggcagg cgccctgag cagcctgag    2100
tacttcagcc tcatgttcga ccgctccgag gtctatggcc ccatgaagaa ataccctcagg    2160
aagcaggtcg aacccctctt ccaacattc gaaactctca ctgccaactg accgagcgc    2220
ccagaaaatc tgatggacca gtacagtgag attaatgcca tcagcactgc ctgctccaat    2280
ggattgcctc aatgtgagaa tctggccaag acccttttcg accagtggat gagcgaccca    2340
gaaaataacc cgatccaccc caacctgcgg tccaccatct actgcaatgc catagccag    2400
ggcggccagg accagtggga cttttgcctgg gggcagttac aacaagccca gctggtaaat    2460
gaggccgaca aactccgctc agcgctggcc tgcagcaacg aggtctggct cctgaacagg    2520
tacctgggtt acaccctgaa cccggacctc attcggaagc aagacgccac ctccactatt    2580
aacagcattg ccagcaatgt catcgggcag cctctggcct gggattttgt ccagagcaac    2640
tggaagaagc tctttcagga ctatggcggt ggttccttct ccttctccaa cctcatccag    2700
ggtgtgaccc gaagattctc ctctgagttt gagctgcagc agctggagca gttcaagaag    2760
aacaacatgg atgtgggctt cggctccggc acccgggctc tggagcaagc cctggagaag    2820
accaaggcca acatcaagtg ggtgaaggag aacaaggagg tggtgttgaa ttggttcata    2880
gagcacagct aa                                                        2892

SEQ ID NO: 9          moltype = DNA   length = 25
FEATURE               Location/Qualifiers
source                1..25
                      mol_type = other DNA
                      organism = synthetic construct
SEQUENCE: 9
caccgctaga aatacctcag gaagc                                           25

SEQ ID NO: 10         moltype = DNA   length = 25
FEATURE               Location/Qualifiers
source                1..25
                      mol_type = other DNA
                      organism = synthetic construct
```

```
SEQUENCE: 10
aaacgcttcc tgaggtattt ctagc                                          25

SEQ ID NO: 11          moltype = DNA  length = 25
FEATURE                Location/Qualifiers
source                 1..25
                       mol_type = other DNA
                       organism = synthetic construct
SEQUENCE: 11
caccgcgagc gcccagaaaa tctga                                          25

SEQ ID NO: 12          moltype = DNA  length = 25
FEATURE                Location/Qualifiers
source                 1..25
                       mol_type = other DNA
                       organism = synthetic construct
SEQUENCE: 12
aaactcagat tttctgggcg ctcgc                                          25

SEQ ID NO: 13          moltype = DNA  length = 21
FEATURE                Location/Qualifiers
source                 1..21
                       mol_type = other DNA
                       organism = synthetic construct
SEQUENCE: 13
gagggcctat ttcccatgat t                                              21

SEQ ID NO: 14          moltype = DNA  length = 20
FEATURE                Location/Qualifiers
source                 1..20
                       mol_type = other DNA
                       organism = synthetic construct
SEQUENCE: 14
caaggatttg tggaggagaa                                                20

SEQ ID NO: 15          moltype = DNA  length = 18
FEATURE                Location/Qualifiers
source                 1..18
                       mol_type = other DNA
                       organism = synthetic construct
SEQUENCE: 15
gctgagcgga gtttgtcg                                                  18
```

PAPN MUTANT AND COMPOSITION FOR SITE-DIRECTED MODIFICATION OF PAPN GENE AND APPLICATION THEREOF

RELATED APPLICATIONS

The present application claims priority from Chinese Application Number 202310706300.0 filed Jun. 14, 2023, the disclosure of which is hereby incorporated by reference herein in its entirety.

INCORPORATION BY REFERENCE

The sequence listing provided in the file entitled pus1232320-2023.10.11.xml, which is an Extensible Markup Language (XML) file that was created on Oct. 11, 2023, and which comprises 27,911 bytes, is hereby incorporated by reference in its entirety.

TECHNICAL FIELD

The present invention relates to the field of gene editing technology, in particular to a pAPN mutant and a composition for site-directed modification of pAPN gene and application thereof.

BACKGROUND

Transmissible gastroenteritis (TGE) is one of the most important diseases that cause morbidity and mortality in piglets, which is a transmissible disease in pigs that must be strictly quarantined as required by the World Organization for Animal Health. TGE is characterized by a short incubation period, rapid transmission speed, and acute onset, so that an infection can be quickly established in a pig herd at various ages from different breeds. Piglets less than 2 weeks old infected with a transmissible gastroenteritis virus (TGEV) have a very high mortality, especially piglets less than 10 days old have a fatality rate up to 100%. Therefore, TGE is considered as one of the important transmissible diseases that harm the pig feeding industry.

TGEV can specifically bind to the host cell, and a S1 moiety of a viral S protein from TGEV as a recognition site can first specifically recognize a receptor on the surface of the host cell, followed by a conformational change in the S protein, so that the virus fuses with the cell membrane. The pAPN protein widely present on the surface of intestinal epithelial cells is an important receptor for TGEV infection in the host cell. Meanwhile, sialic acid as a cofactor plays an important role in the adhesion of TGEV, because sialic acid helps to adhere more virions and promote the virus to cross the mucous layer of intestinal epithelium, so as to protect the virus from emulsification.

However, in addition to playing an important role in mediating TGEV invasion, pAPN also hydrolyzes amide bonds in peptides, amides, and other structures in the small intestine to involve in various peptide metabolisms, thus playing the important role in cell growth, immune regulation, and blood pressure regulation. In addition, the direct knockout of pAPN may affect other physiological functions of the body, as APN is closely related to tumor invasion, migration, immune cell chemotaxis and the like.

A key functional domain or amino acid that mediates the entry of viruses into a host cell by deletion or mutation of a receptor molecule, deprives the receptor of its ability to mediate viruses entry into the cell, while maximizing its function to maintain normal cellular life activities, which is the best strategy to establish TGEV infection resistance targeting a receptor molecule. CRISPR/Cas9 gene editing technology, as a new generation of gene editing technology, can achieve "precise" gene editing, which provides a favorable tool for the construction of a genetically edited pig with TGEV resistance. Therefore, it is particularly important to develop a precisely genetically edited pig with the precise mutation at key sites in pAPN gene, which can maintain normal expression of pAPN protein and resist TGEV infection. This has important scientific and practical significance in pig disease resistance breeding.

In view of this, the present invention is proposed.

SUMMARY OF THE INVENTION

The first objective of the present invention is to provide a pAPN mutant having an alanine at position 734, and the body expressing the pAPN mutant protein has the ability of TGEV resistance.

The second objective of the present invention is to provide a polynucleotide encoding the above pAPN mutant.

The third objective of the present invention is to provide a composition for site-directed modification of pAPN gene.

The fourth objective of the present invention is to provide use of the composition for site-directed modification of pAPN gene.

The fifth objective of the present invention is to provide a preparation method of a cell with site-directed modification of pAPN gene for non-disease diagnostic and therapeutic purposes.

The sixth objective of the present invention is to provide a pAPN mutated cell.

The seventh objective of the present invention is to provide a preparation method of a genetically edited pig for non-diagnostic and therapeutic purposes.

To solve the above technical problems, the present invention especially adopts the following technical solution:

According to one aspect of the present invention, it provides a pAPN mutant having an alanine at position 734.

Preferably, the pAPN mutant is obtained by mutating pAPN with an amino acid sequence set forth in SEQ ID NO: 1, alternatively, comprising an amino acid sequence that is at least 80% identical with SEQ ID NO: 1;

preferably, the pAPN mutant is a polypeptide having a mutation from threonine to alanine at position 734 in the amino acid sequence set forth in SEQ ID NO: 1.

According to another aspect of the present invention, it further provides a polynucleotide encoding the above pAPN mutant.

Preferably, the polynucleotide encoding the mutation at position 734 in pAPN has a sequence of GCC.

According to another aspect of the present invention, it further provides a composition for site-directed modification of pAPN gene, comprising a first sgRNA, a second sgRNA and a donor DNA; and the first and second sgRNAs each target two respective target sites in pAPN gene;

and the donor DNA mutating T734 to A734 in pAPN contains a site-directed modified fragment of an amino acid at position 734 in pAPN gene, which is located between the two respective target sites;

preferably, the nucleotide sequence encoding a gene at position 734 in pAPN gene has a sequence of GCC, which is achieved by the donor DNA;

preferably, the nucleotide sequence of the donor DNA is set forth in SEQ ID NO: 4;

preferably, the nucleotide sequence encoding the first sgRNA is set forth in SEQ ID NO: 2;

preferably, the nucleotide sequence encoding the second sgRNA is set forth in SEQ ID NO: 3.

preferably, the composition comprises a first vector comprising an expression cassette for expressing the first sgRNA and a second vector comprising an expression cassette for expressing the second sgRNA;

preferably, the first vector further comprises an expression cassette for a genetically edited protein;

preferably, the second vector further comprises an expression cassette for a genetically edited protein;

preferably, the genetically edited proteins expressed by the first and second vector independently comprise Cas9, Cas9n, Cpf1, or C2c2, respectively, and further independently preferably Cas9;

preferably, the backbones of the first and second vector are independently derived from pX330, pX260, pX334, pX335, pX458, pX459, pX461, pX462, pX551, or pX552, respectively; and further independently preferably pX458.

According to another aspect of the present invention, it further provides use of the composition for site-directed modification of pAPN gene in any of the following (a) to (e);

(a) constructing a cell line with site-directed modification of pAPN gene for non-disease diagnostic and therapeutic purposes;

(b) preparing a product for prevention of transmissible gastroenteritis in pigs; and (c) constructing a pig model with transmissible gastroenteritis resistance for non-disease diagnostic and therapeutic purposes;

(d) a preparation method of a cell with site-directed modification of pAPN gene; and (e) a preparation method of a genetically edited pig.

preferably, the preparation method of a cell with site-directed modification of pAPN gene comprises that introducing the above composition into a cell of interest to obtain the cell with site-directed modification of pAPN gene;

preferably, the cell of interest is a porcine fibroblast or a porcine ileal epithelial cell;

preferably, a method for introducing comprises electroporation or liposome transfection; further preferably electroporation.

preferably, the cell with site-directed modification of pAPN gene is obtained by screening and identification after the introduction operation;

preferably, the screening comprises screening a monoclonal cell by flow cytometric sorting;

preferably, the identification comprises sequencing or PCR identification;

preferably, PCR identification is performed using primers set forth in SEQ ID NOs: 14-15.

preferably, the pAPN mutated cell expresses the above pAPN mutant; alternatively, it contains the above polynucleotide; alternatively, it is prepared by the above preparation method.

preferably, the preparation method of a genetically edited pig comprises that transplanting the above cell into an enucleated oocyte to obtain a recombinant cloned embryo, which is transplanted into a maternal body for pregnancy to obtain a genetically edited pig with modification of an amino acid at position 734 in pAPN gene; alternatively, the above composition is microinjected into a zygotic embryo in a pig by microinjection to obtain a pAPN gene-modified embryo, which is transplanted into a maternal body for pregnancy to obtain a genetically edited pig with modification of an amino acid at position 734 in pAPN gene;

preferably, a step of identification after birth is further comprised for the genetically edited pig;

preferably, the identification comprises sequencing or PCR identification;

preferably, PCR identification is performed using primers set forth in SEQ ID NOs: 14-15.

preferably, the above composition for site-directed modification of pAPN gene is used for any one of (a) to (e).

The present invention has the following beneficial effects compared with the prior art:

the pAPN mutant provided by the present invention with an alanine at position 734 can maintain its normal expression, while reducing the ability of a host expressing the pAPN mutant to specifically bind to TGEV.

The composition for site-directed modification of pAPN gene provided by the present invention comprises a first sgRNA, a second sgRNA and a donor DNA, which can effectively cleave two target sites in pAPN gene, replacing the amino acid at position 734 located between the two target sites with a site-directed modified fragment of donor DNA, thereby achieving precise mutation of the amino acid at position 734 in pAPN. Based on the precise modification of pAPN gene while capable of avoiding disruption or alteration of the normal expression of other amino acids in pAPN gene, the present invention maximally retains the physiological activity function of pAPN protein on the basis of resisting TGEV infection, and has advantages of wide applicability and high efficiency for gene editing and the like.

The preparation method of a cell with site-directed modification of pAPN gene using the above composition has advantages of simple operation and low cost with accurate modification of the amino acid at position 734 in pAPN gene in the cell. The preparation method of a genetically edited pig obtained by using the pAPN mutated cell has advantages of convenient operation and wide universality, and the prepared pig with gene editing of the amino acid at position 734 have good TGEV resistance while retaining normal expression of pAPN protein.

BRIEF DESCRIPTION OF DRAWINGS

The drawings required in the detailed description or the prior art will be briefly introduced below in order to more clearly illustrate the detailed description of the present invention or the technical solution in the prior art. It is obvious that the drawings described below are some embodiments of the present invention, and other drawings can also be obtained based on these drawings without any creative effort for ordinary persons in the art.

DETAILED DESCRIPTION

Figure 1:
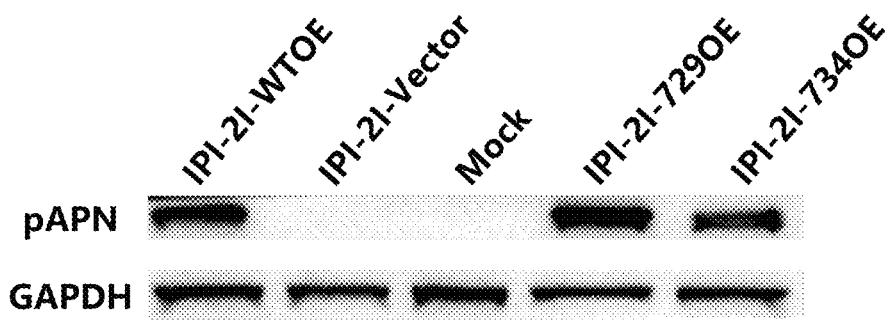
FIG. 1 is an expression graph showing overexpressed pAPN proteins in porcine ileal epithelial cells with precise modification of amino acids at positions 729 and 734 in pAPN gene, as provided in Example 1 of the present invention.

The technical solution of the present invention will be described clearly and completely by combining with examples below, and it is obvious that the described examples are part of the examples in the present invention, but not all of them. Based on the examples in the present invention, all other examples obtained by ordinary technicians in the art without creative efforts fall within the scope of protection of the present invention.

According to one aspect of the present invention, it provides a pAPN mutant having an alanine at position 734. The mutant provided by the present invention is obtained by mutating at position 734 in pAPN with an alanine. The present invention does not limit whether the pAPN without mutation contains other mutation sites, so the precursor of the pAPN mutant provided by the present invention can be a wild-type pAPN or a pAPN mutant that has mutated at other sites based on the wild-type pAPN. The precursor of the pAPN mutant is considered a pAPN protein according to the general definition in the art.

In an optional embodiment, the amino acid sequence of pAPN mutant is set forth in SEQ ID NO: 1, alternatively, comprises an amino acid sequence that is at least 80% identical with SEQ ID NO: 1, for example, but not limited to an amino acid sequence that is at least 80%, 85%, 90%, 95%, or 98% identical with SEQ ID NO: 1.

In an optional embodiment, the pAPN mutant has a mutation from threonine to alanine at position 734 in the amino acid sequence set forth in SEQ ID NO: 1.

According to another aspect of the present invention, it further provides a polynucleotide encoding the above pAPN mutant. "Polynucleotide" herein refers to a polymeric form of a nucleotide including a ribonucleotide and/or a deoxyribonucleotide with any length. Examples of the polynucleotide include, but are not limited to, single-stranded, double-stranded, or multi-stranded DNA or RNA, genomic DNA, cDNA, DNA-RNA heterozygote, or a polymer comprising purine and pyrimidine bases or other natural, chemical, or biochemical modified, unnatural, or derived nucleotide bases. The polynucleotide encodes the above pAPN mutant, which optionally encode a sense or antisense strand. The polynucleotide can be naturally occurring, synthesized, recombinant, or any combination thereof. In an optional embodiment, the polynucleotide encoding the mutation at position 734 in pAPN where an alanine is expressed has a sequence of GCC.

According to another aspect of the present invention, it further provides a composition for site-directed modification of pAPN gene.

The composition comprises a first sgRNA, a second sgRNA and a donor DNA, and the first and second sgRNAs each target two respective target sites in pAPN gene, which can allow the genetically edited protein to target the sequence near the amino acid at position 734 in pAPN gene, but its specific sequence is not defined, as long as allowing for precise targeting function.

In an optional embodiment, the nucleotide sequence encoding the first sgRNA is set forth in SEQ ID NO: 2. In an optional embodiment, the nucleotide sequence encoding the second sgRNA is set forth in SEQ ID NO: 3. The sgRNAs having sequences in SEQ ID NOs: 2 and 3 have more potent targeting and more precise modification.

The composition further comprises a donor DNA containing a site-directed modified fragment of an amino acid at position 734 in pAPN gene that is used to replace the amino acid at position 734 in pAPN gene in order to mutate the amino acid at position 734 in pAPN to A734, thereby achieving sequence recombination, and the site-directed modified fragment is located between two targets targeted by the first and second sgRNAs. The specific sequence of the donor DNA is not defined, as long as allowing for an amino acid mutation at position 734.

In an optional embodiment, the nucleotide sequence encoding a gene at position 734 in pAPN gene has a sequence of GCC, which is achieved by the donor DNA, further preferably, the ACT encoding the amino acid at position 734 in the polynucleotide of pAPN is replaced with GCC by the donor DNA. In an optional embodiment, the nucleotide sequence of the donor DNA capable of accurate replacement of the amino acid at position 734 encoded by pAPN gene with A734 (alanine) is set forth in SEQ ID NO: 4.

In an optional embodiment, the nucleotide sequence encoding the first sgRNA is set forth in SEQ ID NO: 2, the nucleotide sequence encoding the second sgRNA is set forth in SEQ ID NO: 3, and the nucleotide sequence of the donor DNA is set forth in SEQ ID NO: 4 in the above composition.

In the composition for site-directed modification of pAPN gene provided by the present invention, both the first and second sgRNAs can target a fragment of interest that is enzymatically cleaved by the genetically edited protein. Sequence recombination is realized by using donor DNA again. The donor DNA is a replacement template for the modified target sequence of interest, which can specifically recognize the sequence near the amino acid site at position 734 in pAPN gene under the guidance of the first and second sgRNAs. Based on the genetically edited protein, the target fragment is enzymatically cleaved and the donor DNA sequence is guided to replace an original homologous fragment in the cell, thereby achieving the purpose of precise modification of the amino acid at position 734 in pAPN gene. Based on the precise modification of the amino acid at position 734 in pAPN gene while capable of avoiding disruption or alteration of the normal expression of other amino acids in pAPN gene, the present invention maximally retains the physiological activity function of pAPN protein on the basis of resisting TGEV infection, and has advantages of wide applicability and high efficiency for gene editing and the like, which provides strong support for the preparation and breeding of new TGEV-resistant pig varieties with a single amino acid precise mutation in pAPN.

It should be noted that the composition for site-directed modification of pAPN gene provided by the present invention can be used in any form acceptable in the art in combination with a genetically edited protein or a polynucleotides expressing the genetically edited protein. Based on the genetically edited protein, effectively enzymatic cleavage in various cells can be performed and the recombination of the cleaved sequence is guided, which has advantages of wide applicability and high efficiency for enzymatic cleavage. Types of genetically edited proteins are not defined by the present invention, as long as allowing for the genome editing function.

In an optional embodiment, the composition comprises a first vector comprising an expression cassette for expressing the first sgRNA and a second vector comprising an expression cassette for expressing the second sgRNA. In an optional embodiment, the first vector further comprises an expression cassette for a genetically edited protein, and the genetically edited protein expressed by the first vector includes, but are not limited to, Cas9, Cas9n, Cpf1, or C2c2, preferably Cas9. In an optional embodiment, the backbone of the first vector is derived from, for example, but not limited to pX330, pX260, pX334, pX335, pX458, pX459, pX461, pX462, pX551, or pX552, preferably pX458.

In an optional embodiment, the second vector further comprises an expression cassette for a genetically edited protein, and the genetically edited protein expressed by the first vector includes, but are not limited to, Cas9, Cas9n, Cpf1, or C2c2, preferably Cas9. In an optional embodiment, the backbone of the second vector is derived from, for example, but not limited to pX330, pX260, pX334, pX335, pX458, pX459, pX461, pX462, pX551, or pX552, preferably pX458.

Cas9 and pX458 have characteristics of wide universality, good versatility, and high product maturity, thus higher efficiency for enzymatic cleavage can be achieved by using pX458 as the backbone of the vector for gene editing.

In an optional embodiment, the single strands of oligonucleotides with sequences set forth in SEQ ID NOs: 9-10 and SEQ ID NOs: 11-12 is annealed, respectively, in order to form double strands, each of which is linked to the backbone of the enzymatically cleaved vector, and the first and second vectors are obtained by screening for positive clones.

According to another aspect of the present invention, it further provides use of the above composition in any of the following (a) to (e):
(a) constructing a cell line with site-directed modification of pAPN gene for non-disease diagnostic and therapeutic purposes;
(b) preparing a product for prevention of transmissible gastroenteritis in pigs; and
(c) constructing a pig model with transmissible gastroenteritis resistance for non-disease diagnostic and therapeutic purposes;
(d) a preparation method of a cell with site-directed modification of pAPN gene; and
(e) a preparation method of a genetically edited pig.

The site-directed modification of pAPN gene can be achieved by the composition for site-directed modification of pAPN gene provided by the present invention. This system can be used to construct a cell line with site-directed modification of pAPN gene. Since T734 is the most important amino acid site that affects the activity of a TGEV receptor, its point mutation can block the binding of pAPN and TGEV, so as to resist the infection of TGEV, thereby greatly enhancing the body's resistance to TGEV, and constructing a pig with transmissible gastroenteritis resistance. For ease of use, it is prepared into product forms such as a kit and the like.

In an optional embodiment, the preparation method of a cell with site-directed modification of pAPN gene comprises that introducing the above composition for site-directed modification of pAPN gene into a cell of interest to obtain the cell with site-directed modification of pAPN gene. Among them, a method for introducing includes, but are not limited to, electroporation or liposome transfection, preferably electroporation with higher transfection efficiency. The cell of interest includes, but are not limited to, a porcine fibroblast, preferably a porcine fetal fibroblast due to its higher cloning efficiency compared to other cells, or a porcine ileal epithelial cell.

In an optional embodiment, the preparation method further includes obtaining the cell with site-directed modification of pAPN gene by screening and identification after the introduction operation. Preferably, the monoclonal cell is screened by flow cytometric sorting and identified whether it is the cell with site-directed modification at position 734 in pAPN gene, preferably by sequencing.

In an optional embodiment, DNA from the monoclonal cell can be extracted, followed by PCR amplification using primers set forth in SEQ ID NOs: 14-15 to obtain the amplified products, which can be sequenced to confirm whether the cell with precise modification.

In an optional embodiment, the pAPN mutated cell comprises a cell capable of expressing the pAPN mutant in the above embodiment; alternatively, the cell contains the polynucleotide encoding the pAPN mutant in the above embodiment, which can be expressed or not expressed in the pAPN mutated cell, and it can only be replicated but not expressed in the pAPN mutated cell. In an optional embodiment, the pAPN mutated cell is prepared using the preparation method of the above cell with site-directed modification of pAPN gene for non-disease diagnostic and therapeutic purposes.

In an optional embodiment, the preparation method includes transplanting the above pAPN mutated cell into an enucleated oocyte to obtain a recombinant cloned embryo, which is transplanted into a maternal body for pregnancy to obtain a genetically edited pig with modification of an amino acid at position 734 in pAPN gene.

In other optional embodiments, the above composition for site-directed modification of pAPN gene is microinjected into a zygotic embryo in a pig by microinjection to obtain a pAPN gene-modified embryo, which is transplanted into a maternal body for pregnancy to obtain a genetically edited pig with modification of an amino acid at position 734 in pAPN gene In an optional embodiment, a step of identification after birth is further included for the genetically edited pig, preferably, sequencing is used to identify whether the genetically edited pig express the pAPN mutant.

In an optional embodiment, DNA from the genetically edited pig can be extracted, followed by PCR amplification using primers set forth in SEQ ID NOs: 14-15 to obtain the amplified products, which can be sequenced to confirm whether the pig with precise modification.

In an optional embodiment, the above composition for site-directed modification of pAPN gene is used for any one of (a) to (e).

The present invention is further illustrated by specific examples below, but it should be understood that these examples are intended only for more detailed illustration purposes and should not be understood to limit the present invention in any form.

Main Reagents

Collagenase type IV for isolation of porcine fetal fibroblasts were purchased from sigma; DMEM, FBS, PS, NEAA, and Glutamine for cell culture were all purchased from Gibco; the DNA kit for extracting cells and ear tissues was purchased from Tiangen Biotech Co., Ltd.; primers were synthesized by Beijing Tsingke Biotech Co., Ltd.; and the KOD FX PCR enzyme for PCR was purchased from TOYOBO.

Porcine ileal epithelial cells with pAPN gene knockout (Immortal Pig Intestinal-2I Knock Out, IPI-2I-KO) could be found in the reference of "Xu Changjiang, Wang Xiaopeng, Xu Kui et al. Establishment of pAPN gene knockout IPI-2I cell lines Mediated by CRISPR/Cas9 System [J]. China Animal Husbandry and Veterinary Medicine, 2021, 48(7): 2282-2290.DOI:10.16431/j.cnki.1671-7236.2021.07.002.".

Main Instruments $CO_2$ incubator (Thermo Scientific, 3111); clean bench (AIRTECH, SW-CJ-1FD); inverted fluorescence microscope (ZEISS, observerA1); PCR instrument (BIO-RID, C1000 Touch); gel imaging system (BIO-RID, Universal Hood II); micromanipulation system (Eppendorf, Celltram vario); flow cytometric sorter (BD, Aria III).

Example 1 Establishment and Functional Verification of Overexpressed Porcine Ileal Epithelial Cells with Precise Modification of Amino Acids at Positions 729, 734 and 735 in pAPN Gene I. Establishment of overexpressed cells with precise modification of amino acids at positions 729, 734 and 735 in pAPN gene and detection of pAPN expressions in them:
1. CDS sequences of wild-type pAPN gene (SEQ ID NO: 5), as well as pAPN genes with precise modification of amino acids at positions 729, 734 and 735 (SEQ ID NO: 6, SEQ ID NO: 7, SEQ ID NO: 8) named PLVX-WT, PLVX-729, PLVX-734, and PLVX-735, respectively, were separately linked to the backbones of PLVX vectors, followed by plasmid sequencing for future use after expansion.
2. On the day before electrotransfection, porcine ileal epithelial cells with pAPN gene knockout (Immortal Pig Intestinal-2I Knock Out, IPI-2I-KO) were recovered into 10 cm dishes, and the cell transfection could be performed until to about 80% confluence of cells.
3. PLVX-WT, PLVX-729, PLVX-734, PLVX-735, and PLVX empty vector were electrotransfected into IPI-2I-KO cells to obtain successfully overexpressed cells with precise modification, named IPI-2I-WTOE, IPI-2I-729OE, IPI-2I-734OE, IPI-2I-735OE, and IPI-2I-Vector, respectively, for use as donor cells in subsequent TGEV infection experiments.

II. Functional Verification

IPI-2I-WTOE, IPI-2I-729OE, IPI-2I-734OE, IPI-2I-735OE, and IPI-2I-Vector cells obtained in step 1 above were transfected for 24 h, followed by TGEV infection testing with the specific steps as follows:
1. IPI-2I-WTOE, IPI-2I-729OE, IPI-2I-734OE, IPI-2I-735OE, and IPI-2I-Vector cells were inoculated with TGEV virus strains (MOI=1), respectively. Meanwhile, IPI-2I-KO cells without virus inoculation were used as the Mock group.
2. Cells were collected at 12 h after infection, followed by extraction of cell proteins for detection of the expression of pAPN by Western blot. Meanwhile, IPI-2I-KO cells without virus inoculation were used as the Mock group.

Figure 2:
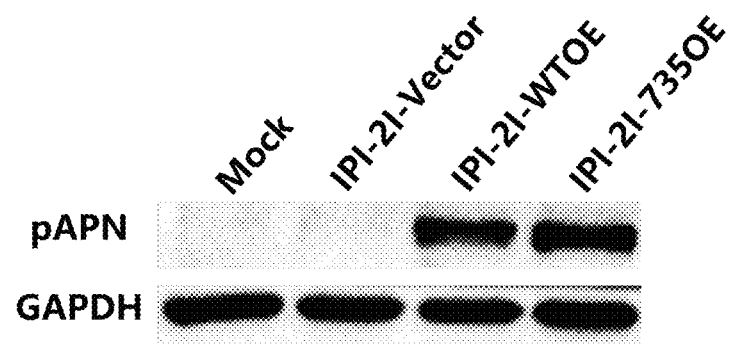
FIG. 2 is an expression graph showing overexpressed pAPN proteins in porcine ileal epithelial cells with precise modification of an amino acid at position 735 in pAPN gene, as provided in Example 1 of the present invention.

The results of pAPN protein detection were shown in FIGS. 1 and 2, indicating that pAPNs were normally expressed in the IPI-2I-WTOE, IPI-2I-729OE, IPI-2I-734OE, and IPI-2I-735OE groups.
3. Cells were collected at 12 h after infection, and washed 4-5 times with PBS, followed by extraction of RNA for detection of the copy number of TGEV virus in cells by qPCR. Meanwhile, IPI-2I-KO cells without virus inoculation were used as the Mock group.

Figure 3:
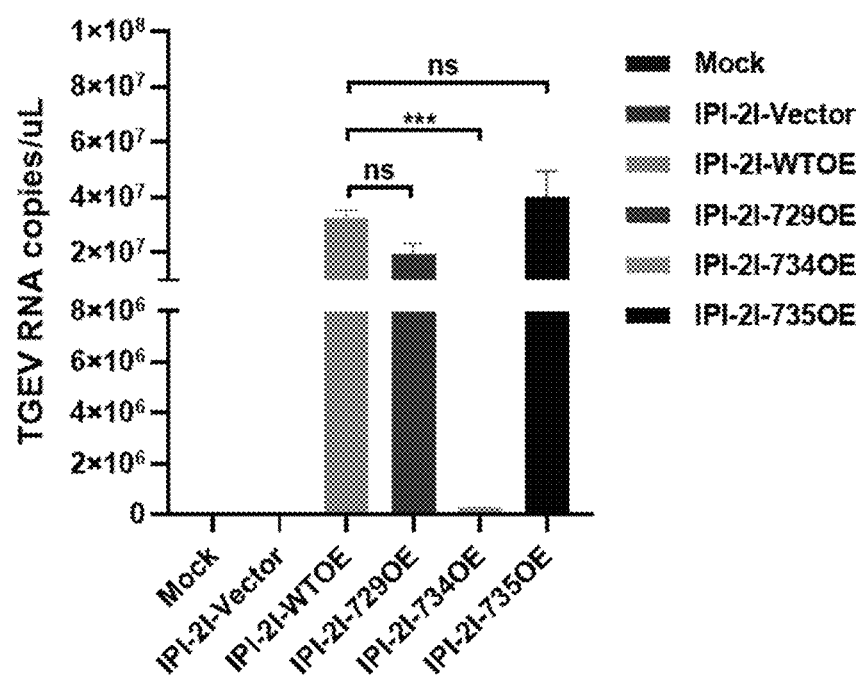
FIG. 3 is a graph of the results of fluorescence quantitative PCR (qPCR) for detection of the copy number of TGEV RNA in overexpressed porcine ileal epithelial cells infected with TGEV, in which amino acids at positions 729, 734 and 735 in pAPN gene are precisely modified, as provided in Example 1 of the present invention.

The qRT-PCR results were shown in FIG. 3, indicating that there were no significant changes in the copy number of TGEV genomic RNA in IPI-2I-729OE and IPI-2I-735OE cells ($P>0.05$), while the copy number of TGEV genomic RNA in IPI-2I-734OE cells was significantly reduced (***$P<0.001$), compared with IPI-2I-WTOE cells.
4. Cells were collected at 12 h after infection, followed by extraction of cell proteins for detection of the expression of TGEV-N protein by Western blot. Meanwhile, IPI-2I-KO cells without virus inoculation were used as the Mock group.

Figure 4:
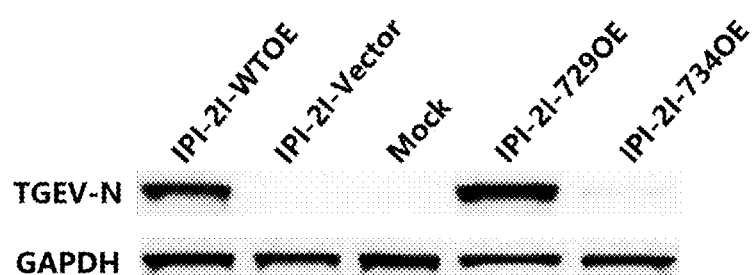
FIG. 4 is a graph of the results of Western Blot for detection of TGEV-N protein in overexpressed porcine ileal epithelial cells infected with TGEV, in which amino acids at positions 729 and 734 in pAPN gene are precisely modified, as provided in Example 1 of the present invention.
Figure 5:
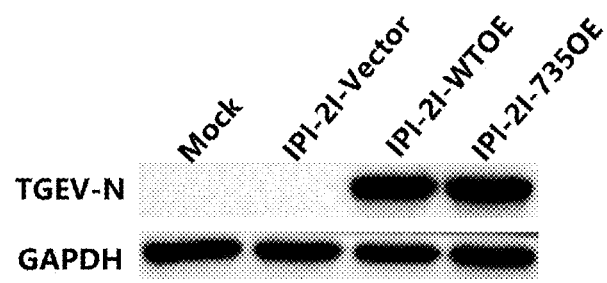
FIG. 5 is a graph of the results of Western Blot for detection of TGEV-N protein in overexpressed porcine ileal epithelial cells infected with TGEV, in which amino acids at position 735 in pAPN gene are precisely modified, as provided in Example 1 of the present invention.

The expression of TGEV-N protein was shown in FIGS. 4 and 5, indicating that there was no significant change in the expression of TGEV-N protein in IPI-2I-729OE and IPI-2I-735OE cells, while the expression of TGEV-N protein in IPI-2I-734OE cells was significantly reduced, compared with IPI-2I-WTOE cells.
5. Cells were collected at 12 h after infection, followed by detection of TGEV infection in cells by indirect immunofluorescence assay (IFA). Meanwhile, IPI-2I-KO cells without virus inoculation were used as the Mock group.

Figure 6:
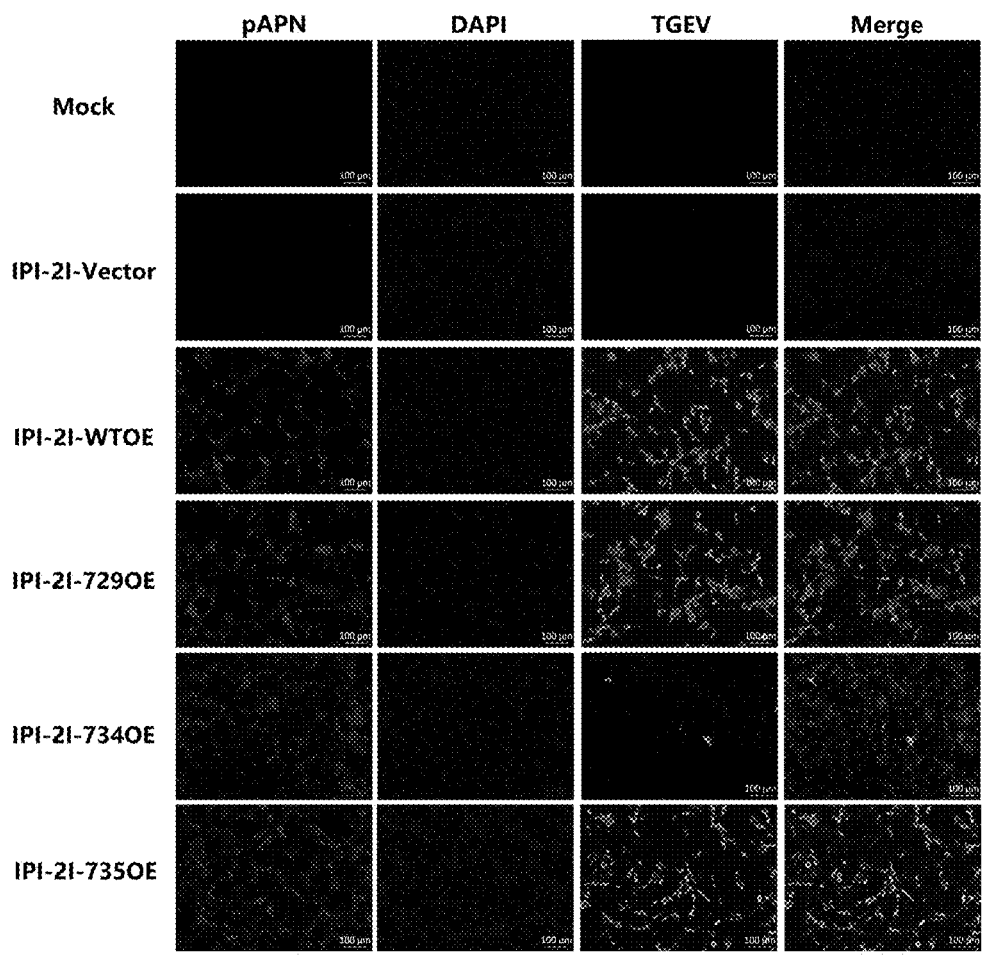
FIG. 6 is a graph of the results of indirect immunofluorescence assay (IFA) for detection of pAPN and TGEV expressions in overexpressed porcine ileal epithelial cells infected with TGEV, in which amino acids at positions 729, 734 and 735 in pAPN gene are precisely modified, as provided in Example 1 of the present invention.

The IFA detection results were shown in FIG. 6, indicating that IPI-2I-WT cells were infected with a large number of TGEVs after virus inoculation; and there was no significant change in the amount of TGEV infection in the IPI-2I-729OE and IPI-2I-735OE groups, while the amount of TGEV infection in IPI-2I-734OE cells was significantly reduced compared with IPI-2I-WT cells.
6. Cells were collected at 12 h after infection, followed by detection of the TGEV virus titer in cells by the TCID50 method. Meanwhile, IPI-2I-KO cells without virus inoculation were used as the Mock group.

Figure 7:
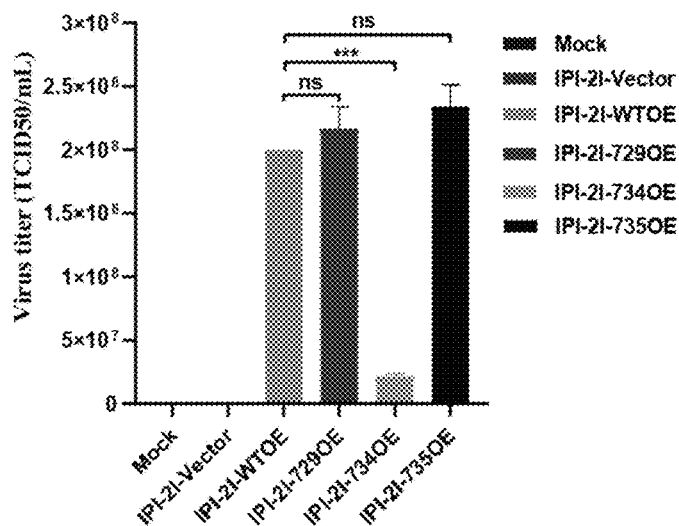
FIG. 7 is a graph of the results of TCID50 detection in overexpressed porcine ileal epithelial cells infected with TGEV, in which amino acids at positions 729, 734 and 735 in pAPN gene are precisely modified, as provided in Example 1 of the present invention.

The TCID50 detection results were shown in FIG. 7, indicating that the TGEV virus titer was higher in IPI-2I-WTOE cells after virus inoculation; there was no significant change in virus titer in IPI-2I-729OE and IPI-2I-735OE cells, while the virus titer in IPI-2I-734OE cells was significantly reduced (***P<0.001) compared with IPI-2I-WT cells.

In summary, the results showed that both overexpressed porcine ileal epithelial cells with precise modification of amino acids at positions 729 and 735 in pAPN gene could not effectively resist TGEV infection, indicating that precise modification at any site in pAPN gene was not sufficient to resist TGEV infection; but overexpressed porcine ileal epithelial cells with precise modification of amino acids at position 734 in pAPN gene could effectively resist TGEV infection, indicating that the position 734 in pAPN gene was a key site for TGEV infection, and the precise modification of the amino acid at position 734 in pAPN gene could effectively resist TGEV infection.

Example 2 Construction of an Expression Vector for a System of Site-Directed Modification at Position 734 in pAPN Gene I. Design of sgRNA Sequence and Construction of a Vector
1. The targeting site that was close to the amino acid site encoding T734 and had a higher score was selected with porcine pAPN gene as the sequence of interest using the sgRNA analysis tool CRISPOR (crispor.tefor.net), as shown below:
Sequence encoding pAPN-sgRNA-1: CTAGAAATACCTCAGGAAGC (SEQ ID NO: 2);
Sequence encoding pAPN-sgRNA-2: CGAGCGCCCAGAAAATCTGA (SEQ ID NO: 3).
sgRNA sequence synthesis:
Synthesis of complementary paired oligonucleotide sequences for pAPN-sgRNA-1 and pAPN-sgRNA-2 sequences:

```
pAPN-sgRNA-1-F:
                                        (SEQ ID NO: 9)
caccgCTAGAAATACCTCAGGAAGC;

pAPN-sgRNA-1-R:
                                       (SEQ ID NO: 10)
aaacGCTTCCTGAGGTATTTCTAGc;

pAPN-sgRNA-2-F:
                                       (SEQ ID NO: 11)
caccgCGAGCGCCCAGAAAATCTGA;

pAPN-sgRNA-2-R:
                                       (SEQ ID NO: 12)
aaacTCAGATTTTCTGGGCGCTCGc.
```

2. Construct the first and second vectors, named pX458-pAPN-sgRNA-1 and pX458-pAPN-sgRNA-2, respectively
(1) The complementary oligonucleotides corresponding to pAPN-sgRNA-1 and pAPN-sgRNA-2 in step 1 were treated at 98° C. for 10 min, respectively, and then naturally cooled to the room temperature for annealing.
(2) The pX458 backbone vector containing Cas9 sequence was cleaved with the restrictive endonuclease Bbs I at 37° C. for 2 h, followed by recovery of the linearized fragments by gel cutting.
(3) The above annealed double-stranded fragments were linked with the backbone of the linearized vector at 16° C. for 1 h, cooled in ice bath for 30 min, followed by heat shock for 45 s, and then transformed into Top10 or DH5α competent cells, which were coated and grown on LB plates containing ampicillin, and single colonies were picked on the next day for culturing and sequencing. Sequencing primers were as follows: U6-FWD: GAGGGCCTATTTCCCATGATT (SEQ ID NO: 13).
(4) The first (pX458-pAPN-sgRNA-1 plasmid) and second (pX458-pAPN-sgRNA-2 plasmid) vectors were extracted and cultured after sequences being correct, and frozen at −20° C. for subsequent cell transfection. The plasmid extraction was carried out using the EndoFree Plasmid Maxi Kit (CoWin Biotech, CW2104M).

II. Design of Donor DNA Sequence and Construction of a Vector

1. Design of Donor DNA Sequence

Figure 8:
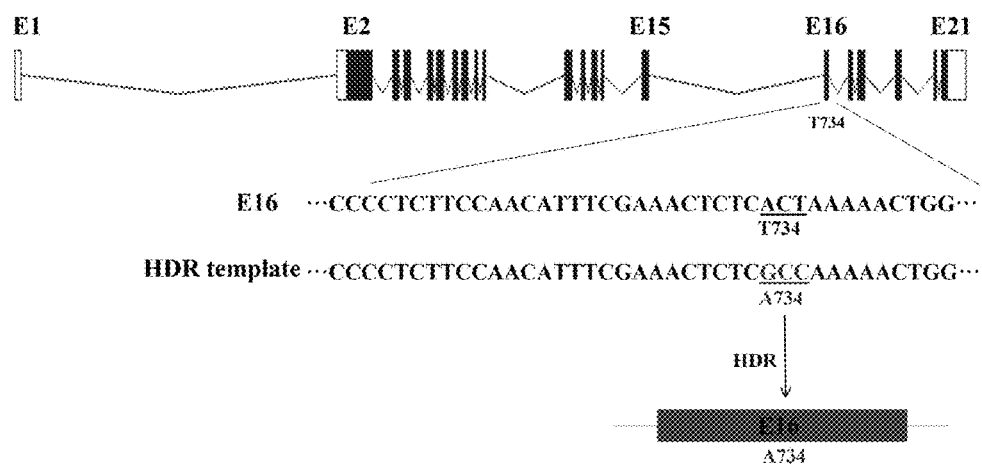
FIG. 8 is a pattern diagram of the precise mutation of an amino acid at position 734 in pig pAPN gene, as provided in Example 2 of the present invention.

Based on the sgRNA sequence, a donor DNA named pAPN-dsODN-734 with its specific sequence set forth in SEQ ID NO: 4 was designed for precise modification of the amino acid at position 734 in pAPN gene. The dsODN sequence shown was used as a double-stranded donor sequence, and when the double-stranded donor sequence replaced the wild-type sequence, T734 was successfully replaced with A734. A pattern diagram of precise mutation of the amino acid at position 734 in pig pAPN gene was shown as FIG. 8.
2. The pAPN-dsODN-734 obtained in part 1 of step II was linked into the PUC57 backbone vector (Genscript Biotech Corporation, SD1176) for sequencing validation, and the correctly sequenced recombinant plasmid was then amplified for subsequent cell transfection. The plasmid extraction was carried out using the EndoFree Plasmid Maxi Kit (CoWin Biotech, CW2104M).

Example 3 Establishment and Functional Verification of the Monoclone from Porcine Ileal Epithelial Cells with Precise Modification of the Amino Acid at Position 734 in pAPN Gene I. Establishment of the Monoclone from Porcine Ileal Epithelial Cells with Precise Modification of the Amino Acid at Position 734 in pAPN Gene Wild-type porcine ileal epithelial cells (IPI-2I-WT) were recovered into a 10 cm dish two days in advance, and the cell transfection could be performed until to 70-80% confluence of cells. 5 μg pX458-pAPN-sgRNA-1 plasmids, 5 μg pX458-pAPN-sgRNA-2 plasmids and 5 μg pAPN-dsODN plasmids were co-transfected into IPI-2I-WT cells with steps following strictly to the instructions of the Basic Primary Nucleofector Kit (Lonza, VPI-1002).

Figure 9:
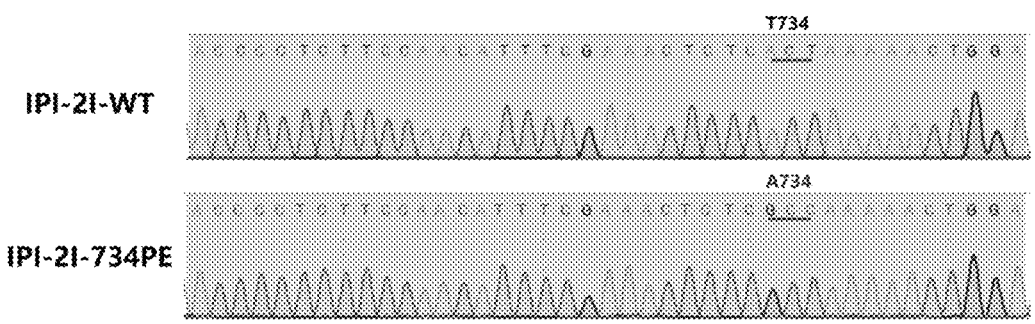
FIG. 9 is a graph of the results of sequencing for a porcine ileal epithelial cell monoclonal with precise modification of an amino acid at position 734 in pAPN gene, as provided in Example 3 of the present invention.
Figure 10:
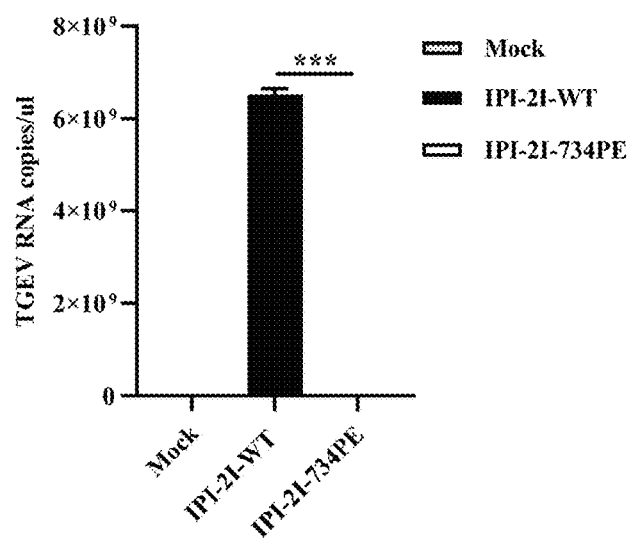
FIG. 10 is a graph of the results of qPCR for detection of the resistance of a porcine ileal epithelial cell with precise modification of an amino acid at position 734 in pAPN gene to TGEV infection, as provided in Example 3 of the present invention.
Figure 11:
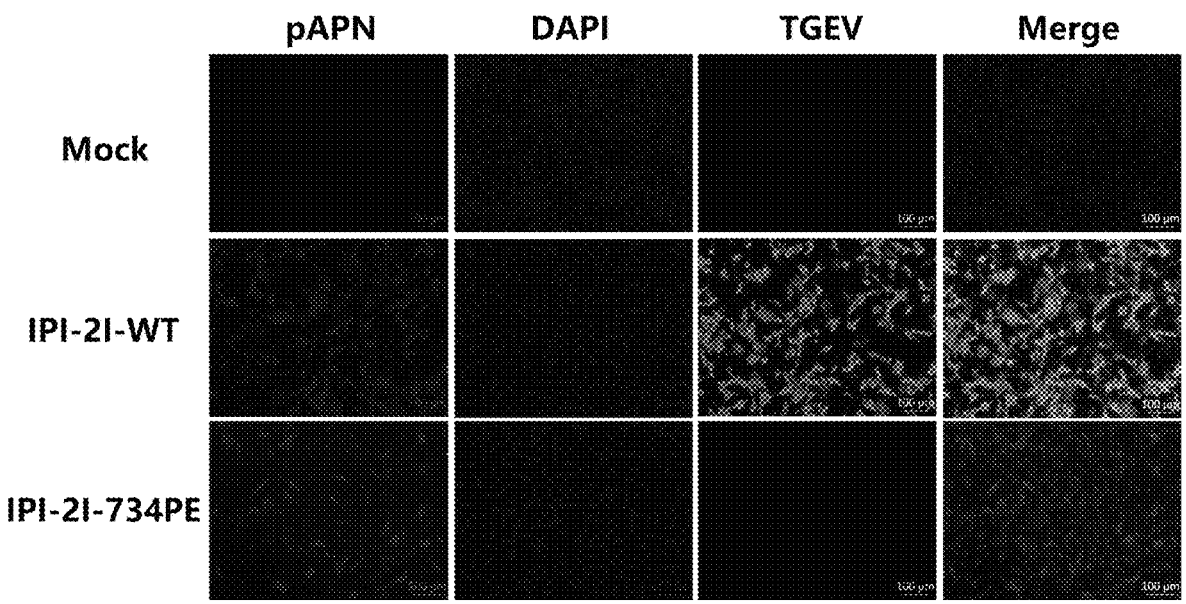
FIG. 11 is a graph of the results of IFA for detection of the resistance of a porcine ileal epithelial cell with precise modification of an amino acid at position 734 in pAPN gene to TGEV infection, as provided in Example 3 of the present invention.
Figure 12:
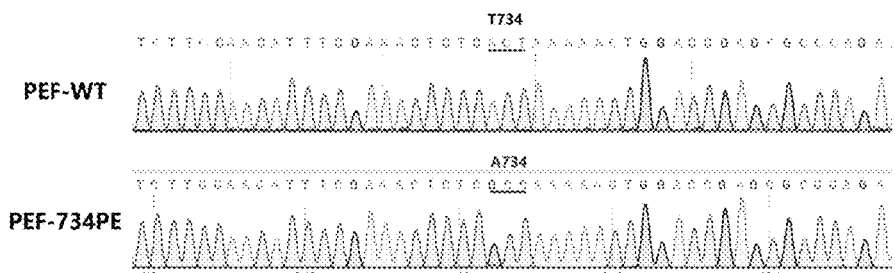
FIG. 12 is a graph of the results of sequencing for a porcine fibroblast with precise modification of an amino acid at position 734 in pAPN gene, as provided in Example 4 of the present invention.

Cells were collected at 48 h after electrotransfection, followed by sorting into 96 well plates using a flow cytometric sorter for culture with the culture medium refreshed every 3 days. After cultivation of the sorted cells for about 10 days, the monoclonal cells were passaged to 48 well plates, and parts of cells were taken for genome extraction and genotype identification until full of cells in 48 well plates. The results showed that IPI-2I (IPI-2I-734PE) cells with precise modification of the amino acid at position 734 in pAPN gene were obtained (FIG. 9), which could be used as donor cells for subsequent TGEV infection experiments.

II. Functional Verification of the Monoclone from Porcine Ileal Epithelial Cells with Precise Modification of the Amino Acid at Position 734 in pAPN Gene IPI-2I-734PE cells obtained above were tested for TGEV infection. IPI-2I-WT and IPI-2I-734PE cells were inoculated with TGEV virus strains (MOI=1), respectively, and IPI-2I-WT cells without virus inoculation were used as the Mock group.

Cells were collected at 12 h after infection, followed by extraction of RNA for detection of the copy number of TGEV virus in cells. The results of qPCR were shown in FIG. 10, indicating that the TGEV genome RNA replicated extensively on IPI-2I-WT cells; the copy number of TGEV genomic RNA in IPI-2I-734PE cells was significantly reduced (***$P<0.001$), compared with IPI-2I-WT cells.

Cells were collected at 12 h after infection, followed by indirect immunofluorescence assay with the results shown as FIG. 11. The results indicated that IPI-2I-WT cells were infected with a large number of TGEVs after virus inoculation; while there was almost no TGEV infection in IPI-2I-734PE cells compared with IPI-2I-WT cells.

The above results showed that the monoclonal porcine ileal epithelial cells with precise modification of amino acids at position 734 in pAPN gene could effectively resist TGEV infection, indicating that the position 734 in pAPN gene was a key site for TGEV infection, and the precise modification of the amino acid at position 734 in pAPN gene could effectively resist TGEV infection.

Example 4 Establishment of the Monoclone From Porcine Fibroblasts with Precise Modification of the Amino Acid at Position 734 in pAPN Gene I. Preparation of Porcine Fetal Fibroblasts The head, tail, limbs, viscera, and bones from a pig embryo at 35 days old were removed, and the blood was cleaned. The fetus was continuously cut using an elbow ophthalmic scissor for 30 min to ensure sufficient fragmentation, and then the fetal tissue fragments were pipetted into a 15 mL centrifuge tube using the head-cutted blue tip, into which 5 mL of complete culture medium were added, followed by natural settlement for a few minutes to remove the supernatant, and a few drops of fetal bovine serum were added to the lower tissue block, which was sucked out using a 15 cm curved glass Pasteur tube bent at 1 cm from the tip, and placed into two T75 culture bottles with the bottom facing upwards, followed by addition of 15 mL of complete culture medium to the opposite side. The culture bottles were carefully turned over after 6-8 h, so that the tissue block was immersed in the culture medium with refreshment every two days to obtain cells, which were frozen and stored for future use until filling the T75 culture bottles. In this process, pigs were fed in the base pig farm of the Beijing Institute of Animal Science of CAAS.

II. Cell Transfection

The primary porcine fetal fibroblasts were recovered into a 10 cm plate at the day before transfection, and the cell transfection could be performed until to about 80% confluence of cells. 5 μg pX458-pAPN-sgRNA-1 plasmids, 5 μg pX458-pAPN-sgRNA-2 plasmids and 5 μg Donor-734 plasmids were co-transfected into porcine fetal fibroblasts with steps following strictly to the instructions of the Basic Primary Fibroblasts Nucleofector Kit (Lonza), and then the electrotransfected cells were transferred to a 6-well plate for culture.

III. Flow Cytometric Sorting and Passage of Monoclonal Cells

Cells were digested and collected into a tube for flow cytometry at 48 h after electroporation. Individual GFP positive cells were sorted using a flow cytometric sorter and cultured in a 96 well plate with refreshment of the culture medium every 3 days. Cells were passaged to a 48 well plate for culture until filling the 96 well plate, and then a portion of cells were taken for genome extraction and genotype identification until filling the 48 well plate.

IV. Identification of Monoclonal Cells

Identification of picked monoclonal cells: the extracted DNA genome was amplified with the upstream and downstream primers set forth in SEQ ID NO: 14 (pAPN-TY-F2 sequence:CAAGGATTTGGAGGAGAA) and SEQ ID NO: 15 (pAPN-TY-R2 sequence:GCTGAGCGGAGTTTGTCG) to obtain a 1443 bp fragment, using the extracted cell genome as a template. The amplification condition was as follows: 94° C. for 5 min; 94° C. for 30 s, 62.6° C. for 30 s, 68° C. for 1 min 40 s, 34 cycles; 72° C. for 5 min. PCR products were sequenced by Beijing Tianyi Huiyuan Company. Based on the results of sequencing, porcine fibroblasts with precise modification of the amino acid at position 734 in pAPN gene were screened as donor cells for nuclear transplantation.

The results of sequencing showed that multiple strains of porcine fibroblasts (PEF-734PE) with precise modification of the amino acid at position 734 in pAPN gene were successfully obtained in this example, and some results of sequencing for the positive cells were shown as FIG. 12.

Example 5 Preparation of a Genetically Edited Pig With Precise Modification of the Amino Acid at Position 734 in pAPN Gene by Somatic Cell Nuclear Transplantation Technology The positive cells obtained from homozygous gene editing in Example 4 were used as donor cells for nuclear transfer, and the enucleated porcine oocytes matured in vitro for 40 h were used as recipient cells for nuclear transfer. The donor cells for nuclear transfer were transferred into the oocytes, which were electrically fused and activated to construct recombinant cloned embryos. The well-developed cloned recombinant embryos were selected and surgically transplanted into the uterus of naturally estrous multiparous white sows for pregnancy. In this process, steps of surgical embryo transfer were as follows: the recipient sow was anesthetized by intravenous injection of Zoletil with a dosage of 5 mg/kg body weight. After anesthesia, the recipient sows were moved to an operating rack for supine fixation, followed by respiratory anesthesia (with a concentration of 3% to 4% isoflurane). An about 10 cm long of surgical incision was made at the midline of the abdomen of the recipient sow to expose ovaries, fallopian tubes, and uterus. An embryo transfer glass tube was used to enter about 5 cm along the fimbria of the fallopian tubes, and the well-developed cloned recombinant embryos were transferred to the junction between the ampulla and isthmus of the fallopian tubes. Embryos were regularly observed by the technicians after transplantation, and the pregnancy statuses of the recipient sows were examined by B-type ultrasound.

Ear tissues were cut from piglets after birth, followed by extraction of genomic DNA, which was amplified by PCR using the above nucleotide sequences of SEQ ID NO: 14 and SEQ ID NO: 15, and the products from PCR amplification were sequenced for genotype detection.

Figure 13:
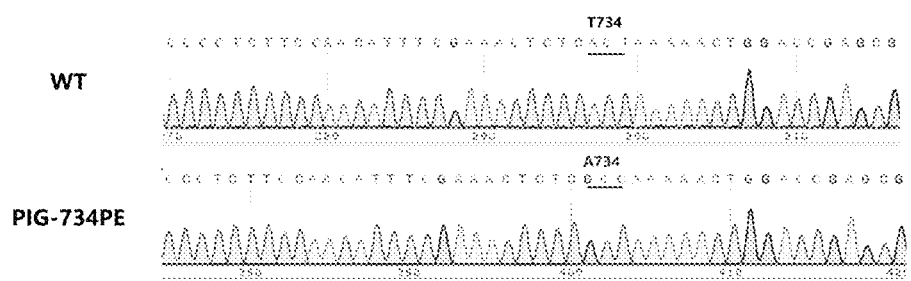
FIG. 13 is a graph of the results of sequencing for a genetically edited pig with precise modification of an amino acid at position 734 in pAPN gene, as provided in Example 5 of the present invention.

The results of sequencing showed that the genetically edited pig (PIG-734PE) with precise modification of the amino acid at position 734 in pAPN gene was successfully obtained in this example, and some results of sequencing for the genetically edited pig were shown as FIG. 13.

Finally, it should be noted that the above examples are only used to illustrate the technical solutions of the present invention and not to limit it. Although the present invention has been described in detail with reference to the above examples, it should be understood by persons of ordinary skill in the art that the technical solutions recorded in the above examples may be modified or equivalently replaced some or all of the technical features. However, these modifications or replacements should not cause the essence of the corresponding technical solutions to deviate from the scope of the technical solutions of various examples in the present invention.

The invention claimed is:

1. A pAPN mutant having an alanine at position 734, wherein the amino acid sequence of the pAPN mutant is forth in SEQ ID NO: 1.

2. A substance comprising:
a polynucleotide encoding the pAPN mutant of claim 1, wherein the polynucleotide encoding the mutation at position 734 in pAPN has a sequence of GCC.

* * * * *